(12) United States Patent
Chen et al.

(10) Patent No.: US 7,470,513 B2
(45) Date of Patent: Dec. 30, 2008

(54) RISK ASSESSMENT FOR ADVERSE DRUG REACTIONS

(75) Inventors: Yuan-Tsong Chen, Taipei (TW);
Shuen-Iu Hung, Chang-Hwa (TW);
Wen-Hung Chung, Nantou (TW);
Jer-Yuarn Wu, Taichung (TW)

(73) Assignee: Academia Sinica, Taipei (TW)

( * ) Notice: Subject to any disclaimer, the term of this patent is extended or adjusted under 35 U.S.C. 154(b) by 302 days.

(21) Appl. No.: 10/705,245

(22) Filed: Nov. 10, 2003

(65) Prior Publication Data
US 2005/0100926 A1   May 12, 2005

(51) Int. Cl.
*C12Q 1/68* (2006.01)
*C12P 19/34* (2006.01)
*C12M 1/34* (2006.01)
*G01N 33/53* (2006.01)

(52) U.S. Cl. .................... 435/6; 435/91.2; 435/287.1; 435/7.1

(58) Field of Classification Search ................. None
See application file for complete search history.

(56) References Cited

U.S. PATENT DOCUMENTS 5,550,039 A * 8/1996 Trachtenberg ............. 435/91.2
6,583,139 B1   6/2003 Thorsett et al.

OTHER PUBLICATIONS

Juppner H 'Functional properties of the PTH/PTHrP receptor'. Bone. Aug. 1995;17(2 Suppl):39S-42S.*
Thisted RA 'What is a P-value?' (1998) available online at http://www.stat.uchicago.edu?~thisted, pp. 1-6.*
Deng et al 'LOD score exclusion analyses for candidate genes using random population samples'. Ann Hum Genet. May 2001;65(Pt 3):313-29.*
Hung et al 'HLA-B genotyping to detect carbamazepine-induced Stevens-Johnson syndrome: implications for personalizing medicine'. Personalized Medicine, Aug. 2005, vol. 2, No. 3, pp. 225-237.*
Carbamazepine, available online at www.mentalhealth.com/drug/p30-t01.html, pp. 1-17.*
Lonjou c et al 'A marker for Stevens-Johnson syndrome . . . : ethnicity matters'. Pharmacogenomics J. Jan. 17, 2006, pp. 1-4.*
Alfirevic A et al 'HLA-B locus in Caucasian patients with carbamazepine hypersensitivity.' Pharmacogenomics. Sep. 2006;7(6):813-8.*
Sankar, P, Nature Genetics (2003), vol. 34, p. 119.*
Wu Y et al 'Activation of T cells by carbamazepine and carbamazepine metabolites', J Allergy CLin Immunol, Jul. 2006, p. 233-241.*
Roujeau JC 'Severe Adverse Cutaneous Reactions to Drugs' NEJM, Nov. 10, 1994, vol. 331:1272-1285.*
Hung S et al 'Genetic susceptibility to carbamazepine-induced cutaneous adverse drug reactions' 2006 Pharmacogenetics and Genomics, vol. 16 No. 4, p. 297-306.*
Saito S et al, Tissue Antigens, 2000, 56:522-529.*
Hoa BK et al, Tissue Antigens, 2007, 71:127-134.*
Chung, W.H., et al. (2004). Medical genetics: a marker for Stevens-Johnson syndrome. Nature. 428(6982):486.
Gumperz, J.E., et al. (1995). The Bw4 public epitope of HLA-B molecules confers reactivity with natural killer cell clones that express NKB1, a putative HLA receptor. J Exp Med. 181(3):1133-1144.
Gut, J. (2002). Severe adverse drug reactions and theragenomics. Business Briefing Pharmatech. Retrieved from the Internet: URL: http://therastrat.com/downloads/Gut_2002_Servere_Adverse_Drug_Reactions.pdf> retrieved on Oct. 1, 2004.
Hildesheim, A., et al. (2002). Association of HLA class I and II alleles and extended haplotypes with nasopharyngeal carcinoma in Taiwan. J Natl Cancer Inst. 94(23):1780-1789.
Mallal, S. et al. (2002). Association between presence of HLA-B*5701, HLA-DR7, and HLA-DQ3 and hypersensitivity to HIV-1 reverse-transcriptase inhibitor abacavir. Lancet. 359(9308):727-732.
Nassif, A., et al. (2002). Drug specific cytotoxic T-cells in the skin lesions of a patient with toxic epidermal necrolysis. J Invest Dermatol. 118(4):728-733.
Pirmohamed, M., and Park, B.K. (2003). Adverse drug reactions: back to the future. Br J Clin Pharmacol. 55(5):486-492.
Romphruk, A., et al. (2003). HLA-B* 15 subtypes in the population of north-eastern Thailand. Eur J Immunogenet. 30(2):153-158.
Bigby M, Jick S, Jick H, Arndt K. (1986) Drug-induced cutaneous reactions. A report from the Boston Collaborative Drug Surveillance Program on 15,438 consecutive inpatients, 1975 to 1982. *JAMA*. 256(24):3358-3363.
Chan SH and Tan T. "HLA and allopurinol drug eruption" *Dermatologica*. 1989, 179(1):32-3.
Edwards SG, Hubbard V, Aylett S, Wren D. Concordance of primary generalised epilepsy and carbamazepine hypersensitivity in monozygotic twins. *Postgrad Med J.* 1999, 75(889):680-1.
Feltkamp TE, Mardjuadi A, Huang F, Chou CT. Spondyloarthropathies in eastern Asia. *Curr Opin Rheumatol.* 2001, 13(4):285-90.

(Continued)

*Primary Examiner*—Jehanne S Sitton
*Assistant Examiner*—Stephen Kapushoc
(74) *Attorney, Agent, or Firm*—Occhiuti Rohlicek & Tsao LLP

(57) ABSTRACT

The present invention provides a method of predicting the risk of a patient for developing adverse drug reactions, particularly SJS or TEN. It was discovered that an HLA-B allele, HLA-B* 1502, is associated with SJS/TEN that is induced by a variety of drugs. The correlation with HLA-B* 1502 is most significant for carbamazepine-induced SJS/TEN, wherein all the patients tested have the HLA-B* 1502 allele. In addition, another HLA-B allele, HLA-B*5801, is particularly associated with SJS/TEN induced by allopurinol. Milder cutaneous reactions, such as maculopapular rash, erythema multiforme (EM), urticaria, and fixed drug eruption, are particularly associated with a third allele, HLA-B *4601. For any of the alleles, genetic markers (e.g., HLA markers, microsatellite, or single nucleotide polymorphism markers) located between DRB1 and HLA-A region of the specific HLA-B haplotype can also be used for the test.

6 Claims, No Drawings

OTHER PUBLICATIONS

Gennis MA, Vemuri R, Burns EA, Hill JV, Miller MA, Spielberg SP. Familial occurrence of hypersensitivity to phenytoin. *Am J Med.* 1991, 91(6):631-4.

Green VJ, Pirmohamed M, Kitteringham NR, Gaedigk A, Grant DM, Boxer M, Burchell B, Park BK. Genetic analysis of microsomal epoxide hydrolase in patients with carbamazepine hypersensitivity. *Biochem Pharmacol.* 1995, 50(9):1353-9.

Hari Y, Frutig-Schnyder K, Hurni M, Yawalkar N, Zanni MP, Schnyder B, Kappeler A, von Greyerz S, Braathen LR, Pichler WJ. T cell involvement in cutaneous drug eruptions. *Clin Exp Allergy.* 2001, 31(9):1398-408.

Khan MA. Update: the twenty subtypes of HLA-B27. *Curr Opin Rheumatol.* 2000;12(4):235-8.

Lazarou J, Pomeranz BH, Corey PN, (1998) Incidence of adverse drug reactions in hospitalized patients: a meta-analysis of prospective studies. *JAMA.* 279(15):1200-1205.

Leeder JS. Mechanisms of idiosyncratic hypersensitivity reactions to antiepileptic drugs. *Epilepsia.* 1998, 39 Suppl 7:S8-16.

Naisbitt DJ, Britschgi M, Wong G, Farrell J, Depta JP, Chadwick DW, Pichler WJ, Pirmohamed M, Park BK. Hypersensitivity reactions to carbamazepine: characterization of the specificity, phenotype, and cytokine profile of drug-specific T cell clones. *Mol Pharmacol.* 2003, 63(3):732-41.

Pichler WJ, Zanni M, von Greyerz S, Schnyder B, Mauri-Hellweg D, Wendland T. High IL-5 production by human drug-specific T cell clones. Int Arch Allergy Immunol. 1997, 113(1-3):177-80.

Pirmohamed M, Lin K, Chadwick D, Park BK. TNFα promoter region gene polymorphisms in carbamazepine-hypersensitive patients. *Neurology.* 2001, 56(7):890-6.

Roujeau JC, Bracq C, Huyn NT, Chaussalet E, Raffin C, Duedari N. HLA phenotypes and bullous cutaneous reactions to drugs. *Tissue Antigens.* 1986, 28(4):251-4.

Roujeau JC, Huynh TN, Bracq C, Guillaume JC, Revuz J, Touraine R. Genetic susceptibility to toxic epidermal necrolysis. *Arch Dermatol.* 1987, 123(9):1171-3.

Roujeau JC. The spectrum of Stevens-Johnson syndrome and toxic epidermal necrolysis: a clinical classification. *J Invest Dermatol.* 1994, 102(6):28S-30S.

Roujeau JC, Stern RS. Severe adverse cutaneous reactions to drugs. *N Engl J Med.* 1994, 331(19):1272-85.

Roujeau JC, Kelly JP, Naldi L, Rzany B, Stern RS, Anderson T, Auquier A, Bastuji-Garin S, Correia-O, Locati F, et al. Medication use and the risk of Stevens-Johnson syndrome or toxic epidermal necrolysis. *N Engl J Med.* 1995, 333(24):1600-7.

Shirato S, Kagaya F, Suzuki Y, Joukou S. Stevens-Johnson syndrome induced by methazolamide treatment. *Arch Ophthalmol.* 1997, 115(4):550-3.

Svensson CK, Cowen EW, Gaspari, AA. (2000) Cutaneous drug reactions. *Pharmacol Rev.* 53(3):357-379.

Wolkenstein P, Carriere V, Charue D, Bastuji-Garin S, Revuz J, Roujeau JC, Beaune P, Bagot M. A slow acetylator genotype is a risk factor for sulphonamide-induced toxic epidermal necrolysis and Stevens-Johnson syndrome. *Pharmacogenetics.* 1995, 5(4):255-8.

Yates CR, Krynetski EY, Loennechen T, Fessing MY, Tai HL, Pui CH, Relling MV, Evans WE. Molecular diagnosis of thiopurine S-methyltransferase deficiency: genetic basis for azathioprine and mercaptopurine intolerance. *Ann Intern Med.* 1997, 126(8):608-14.

* cited by examiner

RISK ASSESSMENT FOR ADVERSE DRUG REACTIONS

FIELD OF THE INVENTION

This invention relates to methods for predicting the risk of an individual for adverse drug reactions.

REFERENCES

U.S. Pat. No. 6,583,139.

Bigby M, Jick S, Jick H, Arndt K. (1986) Drug-induced cutaneous reactions. A report from the Boston Collaborative Drug Surveillance Program on 15,438 consecutive inpatients, 1975 to 1982. JAMA. 256(24):3358-3363.

Chan S H and Tan T. "HLA and allopurinol drug eruption" Dermatologica. 1989,179(1):32-3.

Edwards S G, Hubbard V, Aylett S, Wren D. Concordance of primary generalised epilepsy and carbamazepine hypersensitivity in monozygotic twins. Postgrad Med J. 1999;75(889):680-1.

Feltkamp T E, Mardjuadi A, Huang F, Chou C T. Spondyloarthropathies in eastern Asia. Curr Opin Rheumatol. 2001; 13(4):285-90.

Gennis M A, Vemuri R, Burns E A, Hill J V, Miller M A, Spielberg S P. Familial occurrence of hypersensitivity to phenytoin. Am J. Med. 1991;91(6):631-4.

Green V J, Pirmohamed M, Kitteringham N R, Gaedigk A, Grant D M, Boxer M, Burchell B, Park B K. Genetic analysis of microsomal epoxide hydrolase in patients with carbamazepine hypersensitivity. Biochem Pharmacol. 1995;50(9): 1353-9.

IHWG TECHNICAL MANUAL. Genomic Analysis of the Human MHC. DNA-Based Typing for HLA-Alleles and Linked Polymorphisms. Marcel G. J. Tilanus, Editor in Chief. Distributed by the International Histocompatibility Working Group, ISBN number: 0-945278-02-0.

Hari Y, Frutig-Schnyder K, Hurni M, Yawalkar N, Zanni M P, Schnyder B, Kappeler A, von Greyerz S, Braathen L R, Pichler W J. T cell involvement in cutaneous drug eruptions. Clin Exp Allergy. 2001;31(9):1398-408.

Khan M A. Update: the twenty subtypes of HLA-B27. Curr Opin Rheumatol. 2000;12(4):235-8.

Lazarou J, Pomeranz B H, Corey P N. (1998) Incidence of adverse drug reactions in hospitalized patients: a meta-analysis of prospective studies. JAMA. 279(15):1200-1205.

Leeder J S. Mechanisms of idiosyncratic hypersensitivity reactions to antiepileptic drugs. Epilepsia. 1998;39 Suppl 7:S8-16.

Naisbitt D J, Britschgi M, Wong G, Farrell J Depta J P, Chadwick D W, Pichler W J, Pirmohained M, Park B K. ypersensitivity reactions to carbamazepine: characterization of the specificity, phenotype, and cytokine profile of drug-specific T cell clones. Mol Pharmacol. 2003;63(3):732-41.

Pichler W J, Zarui M, von Greyerz S, Schnyder B, Mauri-Hellweg D, Wendland T. High IL-5 production by human drug-specific T cell clones. Int Arch Allergy Immunol. 1997; 113(1-3):177-80.

Pirmohamed M, Lin K, Chadwick D, Park B K. TNFalpha promoter region gene polymorphisms in carbamazepine-hypersensitive patients. Neurology. 2001;56(7): 890-6.

Roujeau J C, Bracq C, Huyn N T, Chaussalet E, Raffin C, Duedari N. HLA phenotypes and bullous cutaneous reactions to drugs. Tissue Antigens. 1986;28(4):251-4.

Roujeau J C, Huynh T N, Bracq C, Guillaume J C, Revuz J, Touraine R. Genetic susceptibility to toxic epidermal necrolysis. Arch Dermatol. 1987;123(9):1171-3.

Roujeau J C. The spectrum of Stevens-Johnson syndrome and toxic epidermal necrolysis: a clinical classification. J Invest Dermatol. 1994;102(6):28S-30S.

Roujeau J C, Stern R S. Severe adverse cutaneous reactions to drugs. N Engl J. Med. 1994;331(19):1272-85.

Roujeau J C, Kelly J P, Naldi L, Rzany B, Stemr R S, Anderson T, Auquier A, Bastuji-Garin S, Correia 0, Locati F, et al. Medication use and the risk of Stevens-Johnson syndrome or toxic epidermal necrolysis. N Engl J. Med. 1995; 333(24):1600-7.

Shirato S, Kagaya F, Suzuki Y, Joukou S. Stevens-Johnson syndrome induced by methazolamide treatment. Arch Ophthalmol. 1997;115(4):550-3.

Svensson C K, Cowen E W, Gaspari, AA. (2000) Cutaneous drug reactions. Pharmacol Rev. 53(3):357-379.

Wolkenstein P, Carriere V, Charue D, Bastuji-Garin S, Revuz J, Roujeau J C, Beaune P, Bagot M. A slow acetylator genotype is a risk factor for sulphonamide-induced toxic epidermal necrolysis and Stevens-Johnson syndrome. Pharmacogenetics. 1995;5(4):255-8.

Yates C R, Krynetski E Y, Loennechen T, Fessing M Y, Tai H L, Pui C H, Relling M V, Evans W E. Molecular diagnosis of thiopurine S-methyltransferase deficiency: genetic basis for azathioprine and mercaptopurine intolerance. Ann Intern Med. 1997; 126(8): 608-14.

All of the publications, patents and patent applications cited above or elsewhere in this application are herein incorporated by reference in their entirety to the same extent as if the disclosure of each individual publication, patent application or patent was specifically and individually indicated to be incorporated by reference in its entirety.

BACKGROUND OF THE INVENTION

Adverse drug reactions (ADRs) are a major clinical problem. According to a widely cited meta-analysis, ADRs was ranked between the fourth and sixth most common cause of death (Lazarou et al., 1998). In particular, potentially serious cutaneous ADRs account for about 2-3% of all hospital admissions (Bigby et al., 1986). Although drug eruptions may be mild to moderate, such as maculopapular rash, erythema multiforme (EM), urticaria, and fixed drug eruption, more severe cutaneous ADRs are life-threatening and frequently result in death, such as Stevens-Johnson syndrome (SJS) and toxic epidermal necrolysis (TEN; Lyell's syndrome).

SJS is characterized by high fever, malaise, and a rapidly developing blistering exanthema of macules and target-like lesions accompanied by mucosal involvement. TEN has similar presentations with an even more extensive skin detachment and a higher mortality rate (30 to 40%). Although the incidence of SJS/TEN is rare with an annual estimated incidence of 3-5 per million people, these conditions can kill or severely disable previously otherwise healthy people (Roujeau and Stern, 1994). The severity of the condition has prompted pharmaceutical companies to withdraw a few newly released drugs.

Almost all SJS/TEN cases are caused by drugs, most commonly sulfonamides, anticonvulsants, allopurinol, nonsteroidal anti-inflammatory drugs (NSAIDs), and antimalarials (Roujeau et al., 1995). In Taiwan, anticonvulsants (carbamazepine, phenytoin and phenobarbital), and allopurinol are the most common drugs causing SJS/TEN. Other medications such as NSAID and antibiotics are also noted to cause severe ADR.

Recent developments of pharmacogenomics have implied that the susceptibility to ADRs is associated with genetic variants. A successful example of application of pharmacogenomic study to prevent drug-induced side effect is genotyping thiopurine methyltransferase (TPMT) before prescribing azathioprine, a drug for rheumatologic or cancer diseases (Yates et al., 1997). An individual's genomic polymorphism(s) of TPMT can cause enzyme deficiency and slow metabolizing rate, resulting in leukocytopenia. This kind of molecular diagnostics certified by CLIA (Clinical Laboratory Improvement Amendments) is now offered by reference laboratories in the USA (Prometheus Laboratory Inc.; Genaissance Pharmaceutical) and Europe. Although susceptibility to SJS/TEN on certain drugs is thought to be genetically determined (Gennis M A, 1991; Edwards S G, 1999), the responsible genetic factors have yet to be identified and currently there is no method clinically useful that can be used to predict who will develop SJS/TEN or to which drugs.

SUMMARY OF THE INVENTION

The present invention provides a method of predicting the risk of a patient for developing adverse drug reactions, particularly SJS or TEN. It was discovered that an HLA-B allele, HLA-B* 1502, is associated with SJS/TEN that is induced by a variety of drugs. The correlation with HLA-B* 1502 is most significant for carbamazepine-induced SJS/TEN, wherein all the patients tested have the HLA-B*1502 allele. In addition, another HLA-B allele, HLA-B*5801, is particularly associated with SJS/TEN induced by allopurinol. Milder cutaneous reactions induced by carbamazepine, such as maculopapular rash, erythema multiforme (EM), urticaria, and fixed drug eruption, are particularly associated with a third allele, HLA-B*4601.

Accordingly, the present application provides a method of assessing the risk of a patient for developing a cutaneous adverse drug reaction in response to a drug, comprising performing HLA typing using a biological sample from the patient. The drug is preferably selected from the group consisting of carbamazepine, allopurinol, phenytoin, sulfasalazine, amoxicillin, ibuporfen and ketoprofen. Alternatively, the drug is preferably not a nonsteroidal anti-inflammatory drug.

Specifically, one aspect of the present invention provides a method of assessing the risk of a patient for developing an adverse drug reaction in response to a drug, comprising determining the presence of an HLA-B allele selected from the group consisting of HLA-B*1502, HLA-B*5801 and HLA-B*4601, wherein the presence of the HLA-B allele is indicative of a risk for an adverse drug reaction. The drug is preferably selected from the group consisting of carbamazepine, allopurinol, phenytoin, sulfasalazine, amoxicillin, ibuporfen and ketoprofen. Most preferably, the drug is carbamazepine or allopurinol.

The adverse drug reaction is preferably a cutaneous adverse drug reaction, such as Stevens-Johnson syndrome or toxic epidermal necrolysis. In a preferred embodiment, the drug is carbamazepine, and the allele is HLA-B* 1502. In another preferred embodiment, the allele HLA-B*5801 is used to predict the risk for cutaneous ADR, such as Stevens-Johnson syndrome or toxic epidermal necrolysis in response to allopurinol. Other subtypes of HLA-B15, B58 or B46 can also be used to predict the risk for ADR instead of HLA-B*1502, HLA-B*5801 or HLA-B*4601, such as HLA-B*1503.

The allele can be detected by using any method known in the art. For example, the presence of the allele can be determined by using an oligonucleotide that specifically hybridizes with the nucleic acid coding for the allele. Preferably, the DNA prepared from the peripheral blood of the patient is employed in the determination. The allele can also be detected by, for example, serological or microcytotoxicity methods.

The presence of the allele of interest can also be determined by detecting an equivalent genetic marker of the allele, which is a genetic marker that is linked to the allele. For example, the HLA-markers of HLA-B B*1502 haplotype include, without being limited to, DRB1*1202, Cw*0801, Cw*0806, A*1101, and MICA*019. The HLA-markers of the HLA-B*5801 haplotype comprise, for example, Cw*0302. In other words, the presence of the HLA-B*1502, 5801 or 4601 haplotype, rather than the alleles per se, is indicative of a risk for adverse drug reactions.

Another aspect of the present invention provides a method of pharmacogenomics profiling comprising determining the presence of at least one HLA-B allele selected from the group consisting of HLA-B* 1502, HLA-B *5801, and HLA-B*4601. Preferably, the presence of at least two alleles selected from the group is determined, such as HLA-B*1502 and HLA-B*5801. More preferably, the presence of all three alleles is determined. The method can optionally comprise the determination of other genetic factors. Those other genetic factors may be associated with the predisposition for any disease or medical condition, including adverse drug reactions. For example, these other genetic factors may be selected from the group consisting of thiopurine methyltransferase and the genes for the long-QT syndrome.

Further provided is a method of screening and/or identifying medicines that can be used to treat drug-induced SJS/TEN by using HLA-B* 1502, 5801 or 4601 as a target in drug development. For example, cells expressing any of the alleles can be contacted with medicine candidates, and the candidates that bind to the allele are likely to inhibit the function of the allele. The efficacy of the allele-binding candidate in treating drug induced SJS/TEN can then be further tested.

DETAILED DESCRIPTION OF THE INVENTION

The present invention provides a method of predicting the risk of a patient for developing adverse drug reactions, particularly SJS or TEN. It was discovered that an HLA-B allele, HLA-B*1502, is associated with SJS/TEN that is induced by a variety of drugs. The correlation with HLA-B*1502 is most significant for carbamazepine-induced SJS/TEN, wherein all the patients tested have the HLA-B*1502 allele. In addition, another HLA-B allele, HLA-B*5801, is particularly associated with SJS/TEN induced by allopurinol. Milder cutaneous reactions associated with carbamazepine, such as maculopapular rash, erythema multiforme (EM), urticaria, and fixed drug eruption, are particularly associated with a third allele, HLA-B*4601.

Prior to describing the invention in further detail, the terms used in this application are defined as follows unless otherwise indicated.

Definitions

An "adverse drug reaction" is an undesired and unintended effect of a drug. In particular, an adverse drug reaction occurs at doses used for prophylaxis, diagnosis or therapy.

A "drug", or "medication", is any compound or material that is administered to a patient for prophylactic, diagnostic or therapeutic purposes.

A patient has a "risk" for an adverse drug reaction if the probability of the patient to develop an adverse drug reaction is higher than the probability of the general population to develop the adverse drug reaction. The probability of the patient to develop the adverse drug reaction is preferably at least about 1.5 fold, more preferably at least about 2 fold, still more preferably at least about 3, 4, 5, 6, 7, 8 or 9 fold, and most preferably at least about 10 fold as high as the probability of the general population to develop the adverse drug reaction. The probability can be determined by any method known in the art, such as by using the incidence of risk factors. For example, a given risk factor is present in 5% of the general population. If this factor is present in 10% of the patients who have an adverse drug reaction, then the probability of a patient with this risk factor to develop the adverse drug reaction is 2 fold as high as the probability of the general population to develop the adverse drug reaction.

An "equivalent genetic marker" of an allele of interest refers to a genetic marker that is linked to the allele of interest. The useful equivalent genetic markers in the present invention display a linkage disequilibrium with the allele of interest.

"Pharmacogenomics profiling" refers to the determination of genetic factors present in a subject that are associated with diseases or medical conditions, particularly adverse reactions to drugs. Typically, a panel of genetic factors is determined in pharmacogenomics profiling, and the factors may or may not be associated with the same disease, medical condition, or reaction to drug.

A "metabolite" of a drug refers to a compound that can be derived from the drug due to metabolism in a living organism, preferably a mammal, and more preferably a human.

A "derivative" of a drug, as used herein, refers to a compound which is the same as the drug except that at least one hydrogen in the drug is substituted with a halo, hydroxyl, acylamino, alkyl, alkenyl, alkynyl, alkoxy, aryloxy, aryl, aryloxyaryl, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted alkyl, substituted alkoxy, substituted aryl, substituted aryloxy, substituted aryloxyaryl, substituted cycloalkyl, heteroaryl, substituted heteroaryl, heterocyclic or substituted heterocyclic group. The chemical groups are defined below or as defined in U.S. Pat. No. 6,583,139. The substituent contains preferably zero to ten, more preferably zero to six, more preferably zero to four, and most preferably zero to two carbon atoms.

As used herein, "alkyl" refers to alkyl groups preferably having from 1 to 10 carbon atoms and more preferably 1 to 6 carbon atoms. This term is exemplified by groups is such as methyl, t-butyl, n-heptyl, octyl and the like.

"Substituted alkyl" refers to an alkyl group, preferably of from 1 to 10 carbon atoms, having from 1 to 5 substituents selected from the group consisting of alkoxy, substituted alkoxy, acyl, acylamino, thiocarbonylamino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxylaryl, substituted aryloxyaryl, cyano, halogen, hydroxyl, nitro, carboxyl, carboxyalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxylsubstituted heterocyclic, cycloalkyl, substituted cycloalkyl, guanidino, guanidinosulfone thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted aryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR, NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic, mono- and di-alkylamino, mono- and di-(substituted alkyl)amino, mono- and di-arylamino, mono- and di-(substituted aryl)amino, mono- and diheteroarylamino, mono- and di-(substituted heteroaryl)amino, mono- and diheterocyclic amino, mono- and di-(substituted heterocyclic)amino, unsymmetric disubstituted amines having different substituents selected from the group consisting of alkyl, substituted alkyl, aryl, substituted aryl, heteroaryl, substituted heteroaryl, heterocyclic and substituted heterocyclic; substituted alkyl groups having amino groups blocked by conventional blocking groups (such as Boc, Cbz, formyl, and the like) and alkyl/substituted alkyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO₂-heterocyclic, —SO₂-substituted heterocyclic or —SO₂—NRR, where R is hydrogen or alkyl.

"Alkoxy" refers to the group "alkyl-O—" which includes, by way of example, methoxy, ethoxy, n-propoxy, iso-propoxy, n-butoxy, tert-butoxy, sec-butoxy, npentoxy, n-hexoxy, 1,2-dimethylbutoxy, and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acylamino" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic; and where each R can be joined to form, together with the nitrogen atom, a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl group preferably having from 2 to 10 carbon atoms and more preferably 2 to 6 carbon atoms and having at least 1 and preferably from 1-2 sites of alkenyl unsaturation.

"Substituted alkenyl" refers to alkenyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxylcycloalkyl, carboxyl-substituted cycloalkyl, carboxylaryl, carboxyl-substituted aryl, carboxylheteroaryl, carboxyl-substituted heteroaryl, carboxylheterocyclic, carboxylsubstituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)₂-alkyl, —OS(O)₂-substituted alkyl, —OS(O)₂-aryl, —OS(O)₂-substituted aryl, —OS(O)₂-heteroaryl, —OS(O)₂-substituted heteroaryl, —OS(O)₂-heterocyclic, —OS(O)₂-substituted heterocyclic, —OSO₂—NRR, —NRS(O)₂-alkyl, —NRS(O)₂-substituted alkyl, —NRS(O)₂-aryl, —NRS(O)₂-substituted aryl, —NRS(O)₂-heteroaryl, —NRS(O)₂-substituted heteroaryl, —NRS(O)₂-heterocyclic, —NRS(O)₂-substituted heterocyclic, —NRS(O)₂—NR-alkyl, —NRS(O)₂—NR-substituted alkyl, —NRS(O)₂—NR-alkyl, —NRS(O)₂—NR-substituted aryl, —NRS(O)₂—NR-heteroaryl, —NRS(O)₂—NR-substituted heteroaryl, —NRS(O)₂—NR-heterocyclic, —NRS(O)₂—NR-substituted heterocyclic; mono- and di-alkylamino, mono- and di-(substituted alkyl)amino, mono- and di-arylamino, mono- and di-(substituted aryl)amino, mono- and diheteroarylamino, mono- and di-(substituted heteroaryl)amino, mono- and diheterocyclic amino, mono- and di-(substituted heterocyclic)amino, unsymmetric disubstituted amines having different substituents selected from the group consisting of alkyl, substituted alkyl, aryl, substituted aryl, heteroaryl, substituted heteroaryl, heterocyclic and substituted heterocyclic and substituted alkenyl groups having amino groups blocked by conventional blocking groups (such as Boc, Cbz, formyl, and the like) and alkenyl/substituted alkenyl groups substituted with —SO₂-alkyl, —SO₂-substituted alkyl, —SO₂-alkenyl, —SO₂-substituted alkenyl, —SO₂-cycloalkyl, —SO₂-substituted cycloalkyl, —SO₂-aryl, —SO₂-substituted aryl, —SO₂-heteroaryl, —SO₂-substituted heteroaryl, —SO₂-heterocyclic, —SO₂-substituted heterocyclic or —SO₂ NRR, where R is hydrogen or alkyl.

"Alkynyl" refers to alkynyl group preferably having from 2 to 10 carbon atoms and more preferably 3 to 6 carbon atoms and having at least 1 and preferably from 1-2 sites of alkynyl unsaturation.

"Substituted alkynyl" refers to alkynyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted-alkyl, carboxylcycloalkyl, carboxyl-substituted cycloalkyl, carboxylaryl, carboxyl-substituted aryl, carboxylheteroaryl, carboxyl-substituted heteroaryl, carboxylheterocyclic, carboxylsubstituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)₂-alkyl, —OS(O)₂-substituted alkyl, —OS(O)₂-aryl, —OS(O)₂-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic, mono- and di-alkylamino, mono- and di-(substituted alkyl)amino, mono and di-arylamino, mono- and di-(substituted aryl)amino, mono- and diheteroarylamino, mono- and di-(substituted heteroaryl) amino, mono- and diheterocyclic amino, mono- and di-(substituted heterocyclic)amino, unsymmetric disubstituted amines having different substituents selected from the group consisting of alkyl, substituted alkyl, aryl, substituted aryl, heteroaryl, substituted heteroaryl, heterocyclic and substituted heterocyclic; substituted alkynyl groups having amino groups blocked by conventional blocking groups (such as Boc, Cbz, formyl, and the like), and alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic or —SO$_2$ NRR, where R is hydrogen or alkyl.

"Aminoacyl" refers to the groups —NRC(O)alkyl, —NRC(O)substituted alkyl, —NRC(O)cycloalkyl, —NRC(O)substituted cycloalkyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic, where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the groups —NRC(O)O-alkyl, —NRC(O)Osubstituted alkyl, —NRC(O)O-alkenyl, —NRC(O)O-substituted alkenyl, —NRC(O)Oalkynyl, —NRC(O)O— substituted alkynyl, —NRC(O)O-cycloalkyl, —NRC(O)Osubstituted cycloalkyl, —NRC(O)O-aryl, —NRC(O)O-substituted aryl, —NRC(O)Oheteroaryl, —NRC(O)O-substituted heteroaryl, —NRC(O)O-heterocyclic, and —NRC(O)O-substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxycarbonylamino" refers to the groups —OC(O)NRR, —OC(O)NR-alkyl, —OC(O)NR-substituted alkyl, —OC(O)NR-alkenyl, —OC(O)NR-substituent alkenyl, —OC(O)NR-alkynyl, —OC(O)NR-substituted alkynyl, —OC(O)NR-cycloalkyl, —OC(O)NR-substituted cycloalkyl, —OC(O)NR-aryl, —OC(O)NR-substituted aryl, —OC(O)NR-heteroaryl, —OC(O)NR-substituted heteroaryl, —OC(O)NR-heterocyclic, and —OC(O)NR-substituted heterocyclic where R is hydrogen or alkyl, and where each R can be joined to form, together with the nitrogen atom, a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to an unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like). Preferred aryls include phenyl and naphthyl.

Substituted aryl refers to aryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxylsubstituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —SO(O)$_2$-alkyl, —S(O)$_2$-substituted alkyl, —S(O)$_2$-cycloalkyl, —S(O)$_2$-substituted cycoalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-substituted —NRS(O)$_2$—NR-substituted heterocyclic, mono- and di-alkylamino, mono- and di-(substituted alkyl) amino, mono- and di-arylamino, mono- and di-(substituted aryl)amino, mono and di-heteroarylamino, mono- and di-(substituted heteroaryl)amino, mono- and diheterocyclic amino, mono- and di-(substituted heterocyclic)amino, unsymmetric disubstituted amines having different substituents selected from the group consisting of alkyl, substituted alkyl, aryl, substituted aryl, heteroaryl, substituted heteroaryl, heterocyclic, substituted heterocyclic, amino groups on the substituted aryl blocked by conventional blocking groups (such as Boc, Cbz, formyl, and the like), and —SO$_2$NRR, where R is hydrogen or alkyl.

"Aryloxy" refers to the group aryl-O— which includes, by way of example, phenoxy, naphthoxy, and the like.

"Substituted aryloxy" refers to substituted aryl-O— groups.

"Aryloxyaryl" refers to the group -aryl-O-aryl.

"Substituted aryloxyaryl" refers to aryloxyaryl groups substituted with from 1 to 3 substituents on either or both aryl rings selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$— substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic, mono- and di-alkylamino, mono- and di-(substituted alkyl)amino, mono- and di-arylamino, mono- and di-(substituted aryl)amino, mono and di-heteroarylamino, mono- and di-(substituted heteroaryl)amino, mono- and diheterocyclic amino, mono- and di-(substituted heterocyclic)amino, unsymmetric disubstituted amines having different substituents selected from the group consisting of alkyl, substituted alkyl, aryl, substituted aryl, heteroaryl, substituted heteroaryl, heterocyclic and substituted heterocyclic, amino groups on the substituted aryl blocked by conventional blocking groups (such as Boc, Cbz, formyl, and the like) and substituted with —SO$_2$NRR, where R is hydrogen or alkyl.

"Cycloalkyl" refers to cyclic alkyl groups of from 3 to 8 carbon atoms having a single cyclic ring including, by way of example, cyclopropyl, cyclobutyl, cyclopentyl, cyclooctyl and the like. Excluded from this definition are multi-ring alkyl groups such as adamantanyl, etc.

"Cycloalkenyl" refers to cyclic alkenyl groups of from 3 to 8 carbon atoms having single or multiple unsaturation but which are not aromatic.

"Substituted-cycloalkyl" and "substituted cycloalkenyl" refer to a cycloalkyl and cycloalkenyl groups, preferably of from 3 to 8 carbon atoms, having from 1 to 5 substituents selected from the group consisting of oxo(=O), thioxo(=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic, mono- and di-alkylamino, mono- and di-(substituted alkyl)amino, mono and di-arylamino, mono- and di-(substituted aryl)amino, mono- and di-heteroarylamino, mono- and di-(substituted heteroaryl) amino, mono- and di-heterocyclic amino, mono- and di-(substituted heterocyclic)amino, unsymmetric di-substituted amines having different substituents selected from the group consisting of alkyl, substituted alkyl, aryl, substituted aryl, heteroaryl, substituted heteroaryl, heterocyclic and substituted heterocyclic, substituted alkynyl groups having amino groups blocked by conventional blocking groups (such as Boc, Cbz, formyl, and the like) and alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO₂-heterocyclic, —SO₂-substituted heterocyclic or —SO₂ NRR, where R is hydrogen or alkyl.

"Cycloalkoxy" refers to —O-cycloalkyl groups.

"Substituted cycloalkoxy" refers to —O-substituted cycloalkyl groups.

"Halo" refers to fluoro, chloro, bromo and iodo and preferably is either chloro or bromo.

"Heteroaryl" refers to an aromatic carbocyclic group of from 2 to 10 carbon atoms and 1 to 4 heteroatoms selected from the groups consisting of oxygen, nitrogen and sulfur within the ring. Such heteroaryl groups can have a single ring (e.g., pyridyl or furyl) or multiple condensed rings (e.g., indolizinyl or benzothienyl). Preferred heteroaryls include pyridyl, pyrrolyl, indolyl and furyl.

"Substituted heteroaryl" refers to heteroaryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)₂-alkyl, —S(O)₂-substituted alkyl, —S(O)₂-cycloalkyl, —S(O)₂-substituted cycloalkyl, —S(O)₂-alkenyl, —S(O)₂-substituted alkenyl, —S(O)₂-aryl, —S(O)₂-substituted aryl, —S(O)₂-heteroaryl, —S(O)₂-substituted heteroaryl, —S(O)₂-heterocyclic, —S(O)₂-substituted heterocyclic, —OS(O)₂-alkyl, —OS(O)₂'-substituted alkyl, —OS(O)₂-aryl, —OS(O)₂-substituted aryl, —OS(O)₂-heteroaryl, —OS(O)₂-substituted heteroaryl, —OS(O)₂-heterocyclic, —OS(O)₂-substituted heterocyclic, —OSO₂—NRR, —NRS(O)₂-alkyl, —NRS(O)₂-substituted alkyl, —NRS(O)₂-aryl, —NRS(O)₂-substituted aryl, —NRS(O)₂-heteroaryl, —NRS(O)₂-substituted heteroaryl, —NRS(O)₂-heterocyclic, —NRS(O)₂-substituted heterocyclic, —NRS(O)₂—NR-alkyl, —NRS(O)₂—NR-substituted alkyl, —NRS(O)₂—NR-aryl, —NRS(O)₂—NR-substituted aryl, —NRS(O)₂—NR-heteroaryl, —NRS(O)₂—NR-substituted heteroaryl, —NRS(O)₂—NR-heterocyclic, —NRS(O)₂—NR-substituted heterocyclic, mono- and di-alkylamino, mono- and di-(substituted alkyl)amino, mono- and di-arylamino, mono- and di-(substituted aryl)amino, mono- and di-heteroarylamino, mono- and di-(substituted heteroaryl)amino, mono- and di-heterocyclic amino, mono- and di-(substituted heterocyclic)amino, unsymmetric di-substituted amines having different substituents selected from the group consisting of alkyl, substituted alkyl, aryl, substituted aryl, heteroaryl, substituted heteroaryl, heterocyclic and substituted heterocyclic, amino groups on the substituted aryl blocked by conventional blocking groups (such as Boc, Cbz, formyl, and the like), and —SO₂ NRR, where R is hydrogen or alkyl.

"Heteroaryloxy" refers to the group —O-heteroaryl and "substituted heteroaryloxy" refers to the group —O-substituted heteroaryl.

"Heterocycle" or "heterocyclic" refers to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be aryl or heteroaryl.

"Substituted heterocyclic" refers to heterocycle groups which are substituted with from 1 to 3 substituents selected from the group consisting of oxo(═O), thioxo(═S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloakyl, carboxylaryl, carboxyl-substituted aryl, carboxylheteroaryl, carboxyl-substituted heteroaryl, carboxylheterocyclic, carboxylsubstituted heterocyclic, cycloalkyl, substituted cycloalkyl, guanidino, guanidinosulfone, thiol, thioalkyl, substituted thioalkyl, thioaryl, substituted thioaryl, thiocyloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)₂-alkyl, —OS(O)₂-substituted alkyl, —OS(O)₂-aryl, —OS(O)₂-substituted aryl, —OS(O)₂-heteroaryl, —OS(O)₂-substituted heteroaryl, —OS(O)₂-heterocyclic, —OS(O)₂-substituted heterocyclic, —OSO₂—NRR, —NRS(O)₂-alkyl, —NRS(O)₂-substituted alkyl, —NRS(O)₂-aryl, —NRS(O)₂-substituted aryl, —NRS(O)₂-heteroaryl, —NRS(O)₂-substituted heteroaryl, —NRS(O)₂-heterocyclic, —NRS(O)₂-substituted heterocyclic, —NRS(O)₂—NR-alkyl, —NRS(O)₂—NR-substituted alkyl, —NRS(O)₂—NR-alkyl, —NRS(O)₂—NR-substituted aryl, —NRS(O)₂—NR-heteroaryl, —NRS(O)₂—NR-substituted heteroaryl, —NRS(O)₂—NR-heterocyclic, —NRS(O)₂—NR-substituted heterocyclic, mono- and di-alkylamino, mono- and di-(substituted alkyl)amino, mono and di-arylamino, mono- and di-(substituted aryl)amino, mono- and diheteroarylamino, mono- and di-(substituted heteroaryl)amino, mono- and diheterocyclic mono- and di-(substituted heterocyclic)amino, unsymmetric disubstituted amines having different substituents selected from the group consisting of alkyl, substituted alkyl, aryl, substituted aryl, heteroaryl, substituted heteroaryl, heterocyclic and substituted heterocyclic, substituted alkynyl groups having amino groups blocked by conventional blocking groups (such as Boc, Cbz, formyl, and the like) and alkynyl/substituted alkynyl groups substituted with —SO₂-alkyl, —SO₂-substituted alkyl, —SO₂-alkenyl, —SO₂-substituted alkenyl, —SO₂-cycloalkyl, —SO₂-substituted cycloalkyl, —SO₂-aryl, —SO₂-substituted aryl, —SO₂-heteroaryl, —SO₂-substituted heteroaryl, —SO₂-heterocyclic, —SO₂-substituted heterocyclic or —SO₂ NRR, where R is hydrogen or alkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholino, thiomorpholino, piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic.

Methods

There is evidence that the pathogenesis of several similar multisystem drug hypersensitivity reactions involves MHC-restricted presentation of drug or drug metabolites, with direct binding of these non-peptide antigens to MHC molecules or haptenation to endogenous proteins before T cell activation (Svensson et al., 2000). Skin-infiltrating CD8+ cytotoxic T cells were found to be dominant in the bullous reactions such as SJS/TEN (Hari et al., 2001), whereas CD4+ helper T cells were characteristic of milder cutaneous adverse drug reactions, such as maculopapular rash (Pichler et al., 1997). Since the major histocompatibility complex (MHC) is known to be important in determining T-cell mediated immune responsiveness to the antigens, such as metabolites of drugs, we evaluated whether the alleles of the major histocompatibility complex are associated with drug-induced SJS/TEN.

We performed HLA typing on patients with adverse drug reactions (Examples 1-2). The results indicate that HLA-B*1502 was present in 42 of 42 (100%) SJS/TEN patients who received carbamazepine. The allele was also found in 17 of 53 (32%) SJS/TEN-patients who received other drugs (8 phenytoin, 2 allopurinol, 2 amoxicillin, 1 sulfasalazine, 1 ketoprofen, 1 Ibuprofen, and 2 unknown drugs). Particularly, eight of 17 patients (47.05%) who developed SJS/TEN after taking phenytoin also carry the HLA-B*1502 allele. On the other hand, the allele was only found in 4.1% (3/73) of the carbamazepine-tolerant group, 0% (0/32) of the phenytoin-tolerant group, 6.3% (9/142) of the patients who had milder adverse drug reactions other than SJS, and 5.3% (5/94) of the general population. By using the tolerant group as control, the odds ratio, sensitivity, specificity, positive predictive value, and negative predictive value for B*1502 associated carbamazepine-induced SJS/TEN, were 1712, 100%, 95.89%, 96.0%, and 100%, respectively. For B*1502 associated phenytoin-induced SJS/TEN, the odds ratio, sensitivity, specificity, positive predictive value, and negative predictive value were 58, 47%, 100%, 100%, and 65.35%, respectively. Accordingly, the presence of this HLA-B allele can be used in the identification of high-risk patients for drug-induced SJS/TEN, particularly carbamazepine- and phenytoin- induced SJS/TEN.

The mild adverse reactions induced by carbamazepine appear to be associated with another allele, HLA-B*4601. Thus, 10 out of 16 (62.5%) of the patients with these milder reactions to carbamazepine had HLA-B*4601. In contrast, the allele was only found in 26% (19/73) of the carbamazepine-tolerant group. The odds ratio for B*4601 associated carbamazepine-induced milder cutaneous ADRs was 4.73. Consequently, HLA-B*4601 can be used in the risk assessment for mild cutaneous ADR induced by carbamazepine.

A third HLA-B allele, HLA-B*5801, was found in 17 out of 17 (100%) patients with SJS/TEN or hypersensitivity patients who received allopurinol, but only 18% in the general population. The odds ratio, sensitivity, specificity, positive predictive value, and negative predictive value for B*5801 associated allopurinol-induced SJS/TEN or hypersensitivity were 155, 100%, 82%, 84.7%, and 100%, respectively. HLA-B*5801 can thus be used to predict the risk for adverse drug reactions in response to allopurinol.

Accordingly, the present invention provides a method of assessing the risk of a patient for developing an adverse drug reaction after taking a drug, comprising determining the presence of an HLA-B allele selected from the group consisting of HLA-B* 1502, HLA-B*5801 and HLA-B*4601, wherein the presence of the HLA-B allele is indicative of a risk for an adverse drug reaction. In a preferred embodiment, HLA-B* 1502 is used to predict the risk for SJS/TEN, particularly carbamazepine-induced SJS/TEN.

Carbamazepine, also known as Tegretol, Tegol, G-32883, Biston, Calepsin, Carbatrol, Epitol, Finlepsin, Sirtal, Stazepine, Telesmin, or Timonil, is an aromatic anticonvulsant. Other aromatic anticonvulsants, including phenytoin (Dilantin) and phenobarbital, cause similar adverse drug reactions as carbamazepine. Therefore, HLA-B* 1502 can be employed to assess the risk for adverse drug reactions to these other aromatic anticonvulsants as well. The aromatic anticonvulsants for which HLA-B* 1502 can be used as a risk factor also include metabolites and derivatives of carbamazepine, phenytoin or phenobarbital. Metabolites of these drugs are known in the art (see, e.g., Gennis et al., 1991; Leeder, 1998; Naisbitt et al., 2003), such as carbamazepine-10,11 epoxide, carbamazepine-10,11-diol, carbamazepine 2,3-diol, dihydro carbamazepine, carbamazepine catechol and carbamazepine o-quinone, p-hydroxy phenytoin, phenytoin dihydrodiol, phenytoin catechol, phenytoin methylcatechol, and phenytoin o-quinone.

In another preferred embodiment, HLA-B*5801 is used to predict the risk for allopurinol-induced SJS/TEN. Allopurinol is a drug for hyperuricemia and chronic gout. As is with the other drugs, HLA-B*5801 can be used to assess the risk of the metabolites and derivatives of allopurinol as well.

Other subtypes of the HLA-B15, B58 or B46 locus may also be predispositive for cutaneous adverse drug reactions, particularly when the patient is of a different ethnic origin. Such subtype variation has been observed in the art. For example, ankylosing spondylitis is strongly associated with HLA-B27. Many alleles, or subtypes, have been reported for HLA-B27, such as B*2701-B*2723. These subtypes are distributed in different areas in the world and many are associated with ankylosing spondylitis (Khan, 2000; Feltkamp et al., 2001). We contemplate that HLA-B15, B58 or B46 are associated with cutaneous ADR as described herein, and other subtypes of HLA-B15, B58 or B46 may also be used for risk assessment instead of HLA-B*1502, 5801 or 4601, e.g., HLA-B*1503.

Furthermore, it should be noted that in addition to the specific HLA alleles per se, genetic markers that are linked to each of the specific alleles can be used to predict the corresponding ADR risk as well. This is because genetic markers near the HLA allele of interest tend to co-segregate, or show a linkage disequilibrium, with the allele of interest. Consequently, the presence of these markers (equivalent genetic markers) is indicative of the presence of the allele of interest, which, in turn, is indicative of a risk for ADR. As shown in Example 3, the HLA-B*1502 haplotype includes HLA markers such as DRB1*1202, Cw*0801, Cw*0806, A*1101, and MICA*019. The HLA markers of the HLA-B*5801 haplotype include, for example, Cw*0302.

The equivalent genetic marker can be any marker, including HLA markers, microsatellites, and single nucleotide polymorphism (SNP) markers. Preferably, the useful genetic markers are about 200 kb from the HLA-B locus or less. More preferably, the markers are about 100 kb, 80 kb, 60 kb, 40 kb, or 20 kb from HLA-B locus or less. Of particular interest are the markers located between DRB 1 and the HLA-A region of a specific HLA-B haplotype.

The HLA alleles can be detected by using any method known in the art. Preferably, genomic DNA is hybridized to a probe that is specific for the allele of interest. The probe may be labeled for direct detection, or contacted by a second, detectable molecule that specifically binds to the probe. Alternatively, cDNA, RNA, or protein product of the allele can be detected. For example, serotyping or microcytotoxity methods can be used to determine the protein product of the allele. Similarly, the equivalent genetic markers can be detected by any methods known in the art.

To further increase the accuracy of risk prediction, the allele of interest and/or its equivalent genetic marker may be determined along with the genetic markers of accessory molecules and co-stimulatory molecules which are involved in the interaction between antigen-presenting cell and T-cell interaction. These genetic markers include microsatellite, and single nucleotide polymorphism (SNP) markers. The accessory and co-stimulatory molecules include cell surface molecules (e.g., CD80, CD86, CD28, CD4, CD8, T cell receptor (TCR), ICAM-1, CD11a, CD58, CD2, etc.), and inflammatory or pro-inflammatory cytokines, chemokines (e.g., TNF-α), and mediators (e.g., complements, apoptosis proteins, enzymes, extracellular matrix components, etc.). Also of interest are genetic markers of drug metabolizing enzymes which are involved in the bioactivation and detoxification of drugs. These genetic markers also include microsatellite and SNP markers. The drug metabolizing enzymes include phase I enzymes (e.g., cytochrome P450 superfamily etc.), and phase II enzymes (e.g., microsomal epoxide hydrolase, arylamine N-acetyltransferase, UDP-glucuronosyl-transferase, etc.).

The present invention further provides a method for pharmacogenomic profiling. Thus, a panel of genetic factors is determined for a given individual, and each genetic factor is associated with the predisposition for a disease or medical condition, including adverse drug reactions. In the present method, the panel of genetic factors includes at least one allele selected from the group consisting of HLA-B 1502, 5801 and 4601. The panel preferably includes at least two alleles, and most preferably all three alleles, from the group. In addition to HLA-B* 1502, 5801 and/or 4601, the panel may include any other known genetic factors, such as thiopurine methyltransferase and the genes for the long-QT syndrome. The genetic markers for accessory molecules, co-stimulatory molecules and/or drug metabolizing enzymes described above can also be included.

Further provided is a method of screening and/or identifying medicines that can be used to treat drug-induced SJS/TEN by using HLA-B* 1502, 5801 or 4601 as a target in drug development. For example, cells expressing any of the alleles can be contacted with medicine candidates, and the candidates that bind to the allele are likely to inhibit the expression and/or function of the allele. The efficacy of the candidate in treating drug induced SJS/TEN can then be further tested.

Kits

Another aspect of the present invention provides a kit comprising the means for detecting at least one allele selected from the group consisting of HLA-B* 1502, 5801 and 4601. The means is preferably a probe that binds specifically to the allele, and the kit preferably also contains detection reagents for the probe. The probe is preferably an oligonucleotide. The kit may further comprise tools and/or reagents for collecting biological samples from patients, as well as those for preparing genomic DNA, cDNA, RNA or the allele protein from the samples. For example, PCR primers for amplifying the relevant regions of the genomic DNA may be included.

The kit preferably comprises means for detecting at least two alleles selected from the group consisting of HLA-B * 1502, 5801 and 4601. Optionally, the kit may comprise means for detecting other genetic factors as well, particularly those useful in pharmacogenomic profiling. A preferred example is thiopurine methyltransferase.

Thus, in a preferred embodiment, the kit may comprise probes for detecting all three alleles, HLA-B 1502, 5801 and 4601. More preferably, the kit further comprises the PCR primers suitable for each and every allele as well.

The following examples are offered to illustrate this invention and are not to be construed in any way as limiting the scope of the present invention. While this invention is particularly shown and described with references to preferred embodiments thereof, it will be understood by those skilled in the art that various changes in form and details may be made therein without departing from the spirit and scope of the invention as defined by the appended claims.

EXAMPLES

In the examples below, the following abbreviations have the following meanings. Abbreviations not defined have their generally accepted meanings.

°C=degree Celsius hr=hour min=minute sec=second
μM=micromolar
mm=millimolar
M=molar
ml=milliliter
μl=microliter
mg=milligram
μg=microgram
ADR=adverse drug reaction
SJS=Stevens-Johnson syndrome
TEN=toxic epidermal necrolysis
SSO=sequence-specific oligonucleotide
PCR=polymerase chain reaction
HLA=human leukocyte antigen Materials and Methods Patients and Control Subjects A total of 112 SJS/TEN patients were recruited either from Chang Gung Memorial Hospital or from several other medical centers throughout Taiwan. Among these patients, 42 had carbamazepine (tegretol)-induced SJS/TEN and 17 had allopurinol-induced severe ADRs. In addition, 126 patients were also enrolled, who had developed a milder hypersensitivity reaction to various drugs. Drug taking history including dosage and duration, and the phenotypes of adverse drug reactions were recorded. The diagnostic criteria of clinical morphology were defined according to Roujeau (Roujeau J C, 1994). We define SJS as skin detachment of less than 10% of body-surface area, overlap SJS-TEN as skin detachment of 10-30%, and TEN as greater than 30%. SJS, overlap SJS-TEN and TEN are collectively referred to as SJS/TEN.

For each patient, the suspected drug was withdrawn and the patient observed for symptoms. Patients who developed a cutaneous adverse drug reaction that did not subside upon withdrawal of the drug were excluded. 73 tegretol-tolerant patients were included as controls. Volunteers from the general population of Taiwanese (n=94; age range: 20 to 80 years) were also recruited. The study was approved by the institutional review board, and informed consent was obtained.

Genotyping for HLA

Reagents for reverse lineblot sequence-specific oligonucleotide (SSO) were purchased from DYNAL Biotech Ltd. (Bromborough, UK) and used for HLA genotyping. Briefly, a PCR product was generated using biotinylated primer pairs for the second and the third exons of the HLA class I or class II loci, and then hybridized to a lineblot of SSO of probes immobilized on a nylon membrane. The presence of biotinylated PCR product bound to a specific probe is detected using streptavidin-horseradish peroxidase (HRP) and a chromogenic, soluble substrate to produce a blue "line" at the position of the positive probe. The probe reactivity pattern was interpreted by the genotyping software Dynal REL™ SSO(DYNAL Biotech Ltd.; Bromborough, UK). Potential ambiguities were further resolved by sequence-based typing and DNA sequencing performed according to the IHWG Technical Manual (International-Histocompatibility Working Group).

Statistical Analysis

Allele frequencies in the different groups were compared by the Chi-square method with Yates correction by constructing 2×2 tables. P values were corrected for comparisons of multiple HLA alleles (Pc) by multiplying the raw P values by the observed number of HLA alleles present within the loci. Odds ratios were calculated with Haldane's modification, which adds 0.5 to all cells to accommodate possible zero counts.

Example 1

The HLA-B*1502 Allele

In the cohort of 238 individuals with ADRs, 112 cases were diagnosed to have SJS/TEN, and 126 individuals had milder cutaneous adverse drug reactions (erythema multiform, maculopapular rash, urticaria, angioedema, and fixed drug eruption) to various medications. Among the 112 SJS/TEN patients, 42 individuals were exposed to carbamazepine (tegretol), 17 had allopurinol, and 53 were on various medications other than carbamazepine or allopurinol.

The patients were subject to HLA typing as described in Materials and Methods. As shown in Table 1, a DNA variant allele in the HLA-B locus (HLA-B* 1502) was associated in patients with drug-induced SJS/TEN, particularly in patients receiving carbamazepine (tegretol).

TABLE 1

HLA-B*1502 frequency in 42 Taiwanese patients with carbamazepine (tegretol)-induced Stevens-Johnson syndrome/toxic epidermal necrolysis

| Allele | Patients n = 42 | Controls1[a] n = 142 | Controls2[b] n = 94 | Controls3[c] n = 73 | $X^2$ | odds ratio | $P_c$ |
|---|---|---|---|---|---|---|---|
| B*1502 | 42 (100%) | 9 (6.3%) | | | 137.28 | 1194.47 | $3.6 \times 10^{-30}$ |
| B*1502 | 42 (100%) | | 5 (5.3%) | | 110.919 | 1383.2 | $2.15 \times 10^{-24}$ |
| B*1502 | 42 (100%) | | | 3 (4.1%) | 98.936 | 1712 | $9.1 \times 10^{-22}$ |

[a] patients who had milder adverse drug reactions other than SJS
[b] general Taiwanese population
[c] patients who are carbamazepine-tolerant
$X^2$, Chi-square with Yates correction
$P_c$, calculated by multiplying the raw P values by the observed number of HLA-B alleles (35).

Thus, HLA-B*1502 was detected in 42 of 42 (100%) SJS/TEN patients who received carbamazepine. The allele was also found in 17 of 53 (32%) SJS/TEN-patients who received other drugs (8 phenytoin, 2 allopurinol, 2 amoxicillin, 1 sulfasalazine, 1 ketoprofen, 1 Ibuprofen, and 2 unknown drugs). Particularly, eight of 17 patients (47.05%) who developed SJS/TEN after taking phenytoin also carry the HLA-B 1502 allele. On the other hand, the allele was only found in 4.1% (3/73) of the carbamazepine-tolerant group, 0% (0/32) of the phenytoin-tolerant group, 6.3% (9/142) of the patients who had milder adverse drug reactions other than SJS, and 5.3% (5/94) of the general population. By using the tolerant group as control, the odds ratio, sensitivity, specificity, positive predictive value, and negative predictive value for B*1502 associated carbamazepine-induced SJS/TEN, were 1712, 100%, 95.89%, 96.0%, and 100%, respectively. With such a high predictive value and sensitivity, typing of this HLA-B allele can be used in identifying high-risk patients for drug-induced SJS/TEN, particularly tegretol-induced SJS/TEN.

The B*1502 allele does not appear to be associated with all phenotypes induced by tegretol. As shown in Table 2, the allele was not detected in the 16 patients suffering from milder cutaneous reactions to tegretol, such as maculopapular rash (Table 2). However, another allele, HLA-B*4601, is significantly associated with these milder cutaneous reactions (10 out of 16 patients, or 62.5%). Therefore, HLA-B*4601 can be used as a risk factor for mild cutaneous ADRs, particularly those induced by tegretol.

TABLE 2

Phenotype/genotype data of patients with tegretol-induced cutaneous ADRs

| ID | Suspected drug | Phenotype | HLA-B Genotype |
|---|---|---|---|
| 1 | carbamazepine | SJS | B*1502/B*3802 |
| 2 | carbamazepine | SJS | B*1502/B*3501 |
| 3 | carbamazepine | SJS | B*1502/B*4006 |
| 4 | carbamazepine | SJS | B*1502/B*3802 |
| 5 | carbamazepine | SJS | B*1502/B*3802 |
| 6 | carbamazepine, phenytoin | SJS | B*1502/B*3802 |
| 7 | carbamazepine | SJS | B*1502/B*4001 |
| 8 | carbamazepine | SJS | B*1502/B*3901 |
| 9 | carbamazepine | SJS | B 1502/B*5801 |
| 10 | carbamazepine | SJS | B*1502/B*5801 |
| 11 | carbamazepine | SJS | B*1502/B*1525 |
| 12 | carbamazepine | SJS | B*1502/B*4002 |
| 13 | carbamazepine | SJS | B*1502/B*4006 |
| 14 | carbamazepine | SJS | B*1502/B*5801 |
| 15 | carbamazepine | Overlap SJS/TEN | B*1301/B*1502 |
| 16 | carbamazepine | Overlap SJS/TEN | B*1502/B*3501 |
| 17 | carbamazepine | SJS | B*1502/B*3802 |
| 18 | carbamazepine | SJS | B*1502/B*4601 |
| 19 | carbamazepine | SJS | B*1301/B*1502 |
| 20 | carbamazepine | SJS | B*1502/B*5801 |
| 21 | carbamazepine | SJS | B*1502/B*4601 |
| 22 | carbamazepine, NSAID | SJS | B*1502 |
| 23 | carbamazepine | SJS | B*1502/B*3501 |
| 24 | carbamazepine | SJS | B*1502/B*4601 |
| 25 | carbamazepine | SJS | B*1502/B*4601 |
| 26 | carbamazepine | SJS | B*1502/B*5801 |
| 27 | carbamazepine | SJS | B*1501/B*1502 |
| 28 | carbamazepine | SJS | B*1502/B*4001 |

TABLE 2-continued

Phenotype/genotype data of patients with tegretol-induced cutaneous ADRs

| ID | Suspected drug | Phenotype | HLA-B Genotype |
|---|---|---|---|
| 29 | carbamazepine | SJS | B*1502 |
| 30 | carbamazepine, meloxicam, sulidanc, phenytoin | SJS | B*1502/B*5801 |
| 31 | carbamazepine | SJS | B*1502/4601 |
| 32 | carbamazepine | SJS | B*1502/5801 |
| 33 | carbamazepine | SJS | B*1502/4601 |
| 34 | carbamazepine | SJS | B 1502/5502 |
| 35 | carbamazepine | SJS | B*1502 |
| 36 | carbamazepine, phenytoin | SJS | B*1502/4002 |
| 37 | carbamazepine | SJS | B*1502/4001 |
| 38 | carbamazepine | SJS | B*1502 |
| 39 | carbamazepine, phenytoin | SJS | B*1502 |
| 40 | carbamazepine | Overlap SJS/TEN | B*1502/4001 |
| 41 | carbamazepine | Overlap SJS/TEN | B*1502/4601 |
| 42 | carbamazepine | SJS | B*1502/3802 |
| 43 | carbamazepine | maculopapular rash | B*5801/B*4601 |
| 44 | carbamazepine | erythema multiform | B*4001/B*4601 |
| 45 | carbamazepine | maculopapular rash | B*1301/B*4001 |
| 46 | carbamazepine | and angioedema | B*4601/B*5401 |
| 47 | carbamazepine | maculopapular rash | B*4001/B*4601 |
| 48 | carbamazepine, NSAID | maculopapular rash | B*4001/B*4001 |
| 49 | carbamazepine | maculopapular rash | B*1301/B*5502 |
| 50 | carbamazepine | lip swelling, oral and genital ulcer | B*4601/B*5801 |
| 51 | carbamazepine | Maculopapular | B*4601/B*5801 |
| 52 | carbamazepine | and angioedema | B*4001 |
| 53 | carbamazepine | maculopapular rash | B*4001/B*5101 |
| 54 | carbamazepine | maculopapular rash | B*1301/4001 |
| 55 | carbamazepine | maculopapular rash | B*4001/B*4601 |
| 56 | carbamazepine | erythema multiform | B*4601/B*5401 |
| 57 | carbamazepine | maculopapular rash | B*4601 |
| 58 | carbamazepine | erythema multiform | B*4601/5101 |

Example 2

The HLA-B*5801 Allele

We have also identified HLA-B*5801 allele as a risk factor for the development of allopurinol-induced SJS/TEN. The HLA-B*5801 allele was found in all 17 (100%) SJS/severe ADR patients on allopurinol (Tables 3 and 4), but only in 18% of the general Taiwanese population (odds ratio 155, sensitivity 100%, specificity 82%, positive predictive value 84.7%, negative predictive value 100%, Pc=$3.7 \times 10^{-9}$). Accordingly, the HLA-B*5801 allele can be used alone or with other genetic markers for risk assessment for development of SJS in individuals taking allopurinol.

TABLE 3

HLA-B*5801 frequency in 17 Taiwanese patients with allopurinol-induced severe cutaneous adverse drug reactions

| Allele | Patients n = 17 | Controls1[a] n = 142 | Controls2[b] n = 94 | $X^2$ | odds ratio | $P_c$ |
|---|---|---|---|---|---|---|
| B*5801 | 17 (100%) | 26 (18.3%) |  | 47.2 | 153.86 | $2.1 \times 10^{-10}$ |
| B*5801 | 17 (100%) |  | 17 (18.0%) | 41.7 | 155 | $3.7 \times 10^{-9}$ |

[a] patients who had adverse drug reactions other than allopurinol-induced cutaneous ADR
[b] general Taiwanese population
$X^2$, Chi-square with Yates correction
$P_c$, calculated by multiplying the raw P values by the observed number of HLA-B alleles (35).

TABLE 4

Phenotype/genotype data of patients with allopurinol-induced cutaneous ADRs

| Patient ID | Suspected drug | Phenotype | HLA-B Genotype |
|---|---|---|---|
| 59 | allopurinol | SJS | B*0705/B*5801 |
| 60 | allopurinol | SJS | B*4001/B*5801 |
| 61 | allopurinol | SJS | B*1554/B*5801 |
| 62 | allopurinol | SJS | B*3901/B*5801 |
| 63 | allopurinol | SJS | B*5801 |
| 64 | allopurinol | SJS | B*3901/B*5801 |
| 65 | allopurinol | SJS | B*3901/B*5801 |
| 66 | allopurinol | SJS | B*4001/B*5801 |
| 67 | Allopurinol | SJS | B*1502/B*5801 |
| 68 | allopurinol | SJS | B*4001/B*5801 |
| 69 | allopurinol | SJS and vasculitis on leg | B*4601/B*5801 |
| 70 | allopurinol | SJS, and lichenoid | B*4001/B*5801 |
| 71 | allopurinol | SJS | B*4002/B*5801 |
| 72 | allopurinol | SJS | B*4001/B*5801 |
| 73 | alloprinol | SJS | B*5101/B*5801 |
| 74 | allopurinol | TEN | B*1301/5801 |
| 75 | alloprinol | SJS | B*5801 |

Example 3

Equivalent Genetic Markers that are Linked to the HLA-B*1502 or B*5801 Allele

The presence of HLA-B81502, 5801 or 4601 may be indicated by other genetic markers. In particular, genetic markers near the HLA allele of interest tend to co-segregate, or show a linkage disequilibrium, with the allele of interest. Consequently, the presence of these markers (equivalent genetic markers) is indicative of the presence of the allele of interest.

To test the incidence of potential equivalent genetic markers in patients with adverse drug reactions, several markers in the HLA-B*1502 or 5801 haplotype were determined for their association of adverse drug reactions. Indeed, HLA markers of the HLA-B*1502 haplotype, such as DRB1*1202, Cw*0801, Cw*0806, A*1101, and MICA*019, had a significantly higher incidence in SJS/TEN patients who have been exposed to carbamazepine. Similarly, Cw*0302 of the HLA-B*5801 haplotype is associated with allopurinol-induced SJS/TEN (Table 5).

TABLE 5

Contribution of markers of B*1502- and B*5801-ancestral haplotypes to susceptibility to cutaneous adverse drug reactions

|  | CBZ SJS/TEN (n = 42) | CBZ milder (n = 16) | CBZ tolerant (n = 73) | allopurinol SJS/TEN (n = 17) | General population (n = 94) |
|---|---|---|---|---|---|
| HLA-B*1502 | 42 (100%) | 0 (0%) | 3 (4.1%) | 1 (5.8%) | 5 (5.3%) |
| HLA-Cw*0801 | 38 (90%) | ND | 10 (13.7%) | 2 (11.7%) | 10 (10.6%) |
| HLA-Cw*0806 | 3 (7.1%) | ND | 0 (0%) | 0 (0%) | 0 (0%) |
| HLA-A*1101 | 31 (73.8%) | ND | ND | ND | 28 (29.8%) |
| HLA-DRB1*1202 | 35 (83.3%) | ND | ND | ND | 19 (20.2%) |
| HLA-B*5801 | 7 (16.7%) | 3 (7%) | 17 (23%) | 17 (100%) | 17 (18%) |
| HLA-Cw*0302 | 8 (19%) | 2 (16.5%) | 18 (24.6%) | 14 (82%) | 9 (9.5%) |

We claim:

1. A method of assessing a risk of a human patient for developing an adverse drug reaction in response to a drug, comprising
   detecting the presence of an HLA-B*1502 allele in a sample obtained from the patient, and
   correlating the presence of the HLA-B*1502 allele in the sample with an increased risk for an adverse drug reaction in the patient in response to the drug, wherein the adverse drug reaction is Stevens-Johnson syndrome or toxic epidermal necrolysis, and wherein the drug is a carbamazepine.

2. The method of claim 1 wherein the presence of the allele is determined by using an oligonucleotide that specifically hybridizes to the allele.

3. The method of claim 1 wherein the presence of the allele is determined by using DNA prepared from peripheral blood of the patient.

4. The method of claim 1 wherein the presence of the allele is determined by using RNA, protein, cells or sera prepared from peripheral blood of the patient.

5. The method of claim 1, wherein the adverse drug reaction is Stevens-Johnson syndrome.

6. The method of claim 1, wherein the adverse drug reaction is toxic epidermal necrolysis.

* * * * *